(12) United States Patent
Kim et al.

(10) Patent No.: US 6,329,002 B1
(45) Date of Patent: Dec. 11, 2001

(54) FOOD FOR INHIBITING INFECTION AND TREATING GASTRITIS, GASTRIC AND DUODENAL ULCERS

(76) Inventors: Hyun Mi Kim, #202 728-11 Pungdukchunli, Sugieup, Yongin, Kyunggido 449-840 (KR); Cheol Seong Heo, #305 304dong Daelip hansup apt, Chunan, Chungchungnamdo 330-160 (KR); Jung Lyoul Lee, #904 302dong Daewon apt, chowonmayeul pyungchongdong Donganku, Anyang, Kyungkido, 431-070 (KR); Hyung Soo Kim, 52303 Brenton Hills Dr., Granger, IN (US) 46530

( * ) Notice: Subject to any disclaimer, the term of this patent is extended or adjusted under 35 U.S.C. 154(b) by 0 days.

(21) Appl. No.: 09/498,668

(22) Filed: Feb. 7, 2000

(30) Foreign Application Priority Data

Feb. 8, 1999 (KR) .................................................. 99-4234
Sep. 20, 1999 (KR) ................................................ 99-40387

(51) Int. Cl.⁷ .................................................... A01N 63/00
(52) U.S. Cl. .............................. 426/71; 426/61; 426/583; 424/93.4
(58) Field of Search .................................... 426/42, 43, 2, 426/583, 61, 71; 424/93.1, 93.45, 93.4

(56) References Cited

U.S. PATENT DOCUMENTS 5,494,664 * 2/1996 Brassart et al. ..................... 424/93.4

FOREIGN PATENT DOCUMENTS 0877032   11/1998   (EP) .
4275232   9/1992    (JP) .

OTHER PUBLICATIONS

Lee et al., "Effect of Bifidobacterium longum HY8001 administration on human . . . ", Korean Journal of Applied Microb. & Biotech., 27(4):267–272, abstract, Jan. 1999.*

* cited by examiner

Primary Examiner—Keith Hendricks
(74) Attorney, Agent, or Firm—Alfred D. Lobo

(57) ABSTRACT

Live strains of Lactococcus sp. HY 49, *Lactobacillus casei* HY 2782, and *Bifidobacterium longum* HY 8001 maintained in nutritious foods, such as yogurt, imbue them with prophylactic and/or therapeutic properties. Such foods are beneficial in the prevention and/or treatment of gastritis, duodenal and gastric ulcers caused by infection from *Helicobacter pylori* (also referred to as *H. pylori*). The properties of these bacteria are boosted by the addition of egg yolk containing antibodies specific to *H. pylori* antigen derived from "fractionated *H. pylori*".

16 Claims, 1 Drawing Sheet

FOOD FOR INHIBITING INFECTION AND TREATING GASTRITIS, GASTRIC AND DUODENAL ULCERS

FIELD OF THE INVENTION

A nutritional formulation in which non-toxic (to humans) bacteria thrive, is used to prevent and treat gastric disorders associated with *Helicobacter pylori* (also referred to as *H. pylori*) which are attacked by the non-toxic bacteria. Only particular strains of non-toxic comestible bacteria, when ingested by humans are effective against *H. pylori*. Optionally and preferably, the prophylactic and/or therapeutic effects of the comestible bacteria are boosted with egg yolk containing immunoglubins (antibodies) specific to *H. pylori* antigen (also referred to as "*H. pylori*-antibodies").

BACKGROUND OF INVENTION

Much has been published regarding *H. pylori* which inhabits the human gastric mucosa. It is a gram-negative spiral rod-shaped bacterium having an outer membrane with four to six polar flagella which are sheathed and have bulbous ends; each *H. pylori* bacterium is about 0.85 $\mu$m (micrometer) in diameter with an average length of 2.9 $\mu$m. Known pathogenic (disease) factors of *H. pylori* are (i) urease which is produced by the bacteria to allow it to thrive in a strong acid environment in the range from pH 1–3, (ii) flagella which provide the bacteria with mobility, and (iii) a proteinaceous outer membrane of the cells which membrane helps the cells to stick to the gastric mucosal cells.

To date, treatment to subdue secretion of gastric acid, for example with H2 isolator, is deemed unsatisfactory over the long term due to recrudescence which is now countered with medicines which act directly on the *H. pylori*. Presently, trends in the fight against infection by *H. pylori* may be categorized as follows: (a) development of antibiotics showing a direct effect against *H. pylori*, (b) development of vaccines for *H. pylori*, and (c) using anti-*H. pylori* antibodies which allow the live *H. pylori* to be terminated. For prophylaxis, (b) and (c) are preferred.

Bhatia et al in *J. Clin. Microbiol.* 27: 2328–2330, 1989, disclosed that *L. acidophilus* could inhibit the growth of *H. pylori* in vitro, and that this effect was due to lactic acid. Midolo et al in *J. Appl. Bacteriol.* 79:475–479, 1995, disclosed that *L. casei, L. bulgaricus, Pediococccus pentosaceus* and *Bifidobacterium bifidus* could inhibit the growth of *H. pylori* in vitro, and that this effect was due to organic acids produced by these bacteria. However, as stated in European Patent Application EP 0 877 032 A1 to Kodama et al (hereafter, "the '032 application"), one cannot expect experiments conducted in vitro to be replicated in the stomach. An attempt to use *Lactobacillus salivarius* as a probiotic to inhibit growth of *H. pylori* is reported by Aiba et al in *The Meeting of the 30th Japan Germ-free Animal Gnotobiology Society*, Program and Abstracts, pp 22, Requested Title 18, "New Attempt for Inhibiting *H. pylori*" (January 1997). They also used anti-*H. pylori* antibodies in the yolks of eggs of hens immunized with formalin-killed, whole *H. pylori* cells. In germ-free mice, the effectiveness of the *L. salivwius* was 2 to 3 orders of magnitude greater than that of the antibodies; effectiveness in the environment of the stomach of a mammal such as a normal mouse, or in the pH 1-3 of a human, was not investigated. Though the particular strain of *L. salivarius* was not identified, there is no reason to believe that any lactic acid bacteria will be comparably effective even in a germ-free mouse; data presented below indicate that several species of Lactobacillus show high in vitro activity, but are not as effective in vivo as others with comparably high in vitro activity. In particular, certain strains of *L. casei* are insubstantially effective in vitro relative to one found to be quite effective both in vitro and in vivo; only the strain HY 2782 lodge in the Korean Culture Collection, Seoul, Republic of Korea under Depository No KFCC-10803 was found sufficiently effective to be useful in a food, as shown in the comparison below.

In the prior art there are taught many immunization schedules under which growth of anti-*H. pylori* antibodies can be stimulated, most relevant among which are the disclosures of Japanese Patent Application Kokai No. 4-275232 to Takahashi et al, which discloses antibodies obtained in eggs of hens immunized against *H. pylori* whole cells as an antigen; and, the disclosure of the '032 application which discloses antibodies obtained in eggs of hens immunized against (i) flagella of *H. pylori* separated from the rest of the cells; and (ii) urease of *H. pylori* separated from the rest of the cells, these being pathogenic factors associated with *H. pylori*. Antibodies obtained from either (i) or (ii), by themselves, had no noticeable effect on the number of cells in the stomach of five mice; however, (i) and (ii) in combination eliminated the *H. pylori* cells from the stomachs of 5 out of 5 mice. (see Table 2 in the '032 application).

Takahashi et al teach the use of a solution of shattered or comminuted *H. pylori* as antigen, but the beneficial effects are relatively small because the solution additionally contains many other different proteins which appear to dilute, if not diminish or negate, the ability of the antigen to generate effective antibodies.

Furthermore, Kodama et al teach that either the anti-urease antibodies or the anti-flagella antibodies, or both together, may be used in combination with at least one organism selected from the group consisting of lactic acid bacteria, Enterococci, yeasts and Bacillus to inhibit the growth of *H. pylori* in the stomach, teaching that the presence of any live organism unexpectedly enhances the effectiveness of the antibodies, though the live organism, by itself, was ineffective in the environment of the stomach. In particular, Kodama states that *L. acidophilus, L. casei, L. bulgaricus, Pediococcus pentosaceus* and *Bifidobacterium bifidus* were all reported to inhibit growth of *H. pylori* in vitro purportedly due to organic acids produced by these bacteria, but such effectiveness was of no help to assess the effect in the stomach. Evidence of the synergistic effect of antiurease antibodies and *Lactobacillus acidophdus* administered in combination orally to *H. pylori*-infected mice is presented in Table 3 of EP '032. Note however, that only one-half of the population of *L. acidophilus* is found after 14 days. Without considering the propriety of extrapolating those results to all live organisms tested, it is evident from results presented in Table 3 that one particular strain of *L. acidohilus* showed a synergistic effect with *H. pylori*-urease. However, one skilled in the art is unable, without undue experiment-ation, to reproduce the effect reported, because it is not reasonably possible to find the single strain among all the known strains of *L. acidophilus* which produces the synergistic result.

Confirmation of the ineffectiveness of the live organism, by itself, is stated as follows: "*L. acidophilus* alone was almost the same as that of the control group, and there was no significant difference between the two groups, as shown in Table 3. Also, gastritis conditions were observed and *L. acidophilus* had no efficacy on suppressing gastritis." (see page 10, lines 49–52). The tests were performed on hairless mice (NS:Hr/ICR) having a high sensitivity to *H. pylori* infection. Such mice do not have the normal flora found in a BALB/c mouse which provides a better comparison with a human stomach.

Contrary to Kodama's teaching, we found that to get the beneficial effects of a bacteria in vivo in the stomach, it is critical that we use a live bacteria which by itself is highly effective in vitro against *H. pylori*—and to boost its effect, to use antibodies produced by antigens of fractionated *H. pylori*. The term "fractionated *H. pylori*" refers to particular portions of *H. pylori* which portions are separated from the remainder of the cells; the separated portions are as follows: (i) urease; (ii) the outer membrane and (iii) the flagella; the remainder of the cells is discarded. Since it is not practical to conduct a very large number of in vivo experiments with *H. pylori*-infected mice using strains of various bacteria, we chose to use a combination of the three strains found after screening a limited number of strains set forth in Table 1 below. It is recognized that there may be one or more specific strains of *L. acidophilus*, not suggested in the '032 application, any one of which, by itself, may be effective against *H. pylori* not only in vivo but also in vitro; they chose to use a strain which was effective in neither.

It is now evident that, in the prior art, the problem of attacking the *H. pylori* in a stomach relied upon the *H. pylori*-antibodies collected from one or more constituents of fractionated *H. pylori*; or, in combination with a bacteria such as *L. acidophilus* used in the '032 application, or any other bacteria which by itself had no noticeable effect in the environment of a stomach. The invention described hereunder derived from the notion that some bacteria ingested by humans might survive the environment of the stomach for long enough to find the relatively less acidic zones around *H. pylori* attached in the stomach's lining, and excrete bacteriocins which would attack the *H. pylori*. A search was made for those bacteria which could be relied upon to provide a major portion of the desired attack, their effectiveness being supplemented with conventionally derived *H. pylori*-antibodies.

Further, the prior art typically obtained egg yolk powder by freeze-drying an aqueous solution, and was unconcerned with formulating a commercially marketable food fortified with egg yolk powder containing *H. pylori*-antibodies; this led to a lack of concern to stabilize the antibodies during spray-drying of egg yolk solution to make the powder, spray-drying to sterilize being the preferred commercial method of production of egg yolk powder. Sterilization requires spray-drying at a temperature of at least 65° C. at which temperature the antibodies are unstable. The prior art did not provide a solution to the problem of finding a comestible, non-toxic water-soluble food ingredient which is able to stabilize the antibodies in the egg yolk solution at a pH and temperature which would not deleteriously affect the antibodies.

Despite the development of several medicines for the treatment of disorders due to *H. pylori*, the prior art has failed to suggest any logical basis for selecting an active strain of non-toxic, live bacteria for such treatment, except trial and error. By "active strain" is meant a non-toxic strain of live bacteria which effectively kills or inhibits the growth of *H. pylori* grown as a lawn in a growth-conducive anaerobic or microaerophilic environment, on a medium in vitro, in an amount sufficient to provide a zone free of *H. pylori*, which zone is visually observable with the naked eye. Particularly because it is not possible to predict whether an active strain which produces the appropriate bacteriocins will survive long enough to be effective in the environment of a human stomach, we chose to study lactic acid bacteria, and closely related bacteria, which are beneficial and known to survive in the stomach of a human body; and, if specific strains of those bacteria produced the appropriate *H. pylori*-specific bacteriocins, sought to deliver the bacteria in food routinely consumed by humans in everyday life.

SUMMARY OF THE INVENTION

A natural or synthetic food is supplemented with particular strains of live bacteria which by themselves are effective against *Helicobacter pylori* (also referred to as *H. pylori*) not only in vitro but in vivo. Optionally and preferably, the effectiveness of such bacteria is boosted with egg yolk containing antibodies specific to *H. pylori* antigens, so that consuming the food will prevent and/or treat gastritis, and/or gastric and duodenal ulcers.

It has been discovered that specific strains of non-toxic (to humans) live bacteria, by themselves, when maintained as "active strains" in comestible foods, such as yogurt and other bacteria-tolerant foods which may contain other living organisms, have the unique ability to imbue such foods with prophylactic and/or therapeutic properties because, it is hypothesized, active strains produce bacteriocins which directly attack *H. pylori*. In the genus of lactic acid bacteria, only the strains Lactococcus sp. HY 49, Lactobacilhus caseiHY 2782; and in the genus of Bifidobacterium which is closely related to lactic acid bacteria, only the strain *Bifidobacterum longum* HY 8001; lodged in the Korean Culture collection, Seoul, Republic of Korea under Depository No. KFCC 10870 for convenience these three together are referred to herein as "active lactic acid bacteria strains" because they have been found either to minimize the growth of, or to destroy *H. pylori* not only in vitro but also in vivo in the environment of a stomach, provided each strain is used, either individually or in combination, in an effective dosage amount.

It is therefore a general object of this invention to provide a food for general human consumption, comprising a food stored at a temperature in the range from about −45° C. but no more than 45° C. and effective to inhibit and/or prevent the growth of *H. pylori* in a human stomach; the food is most preferably of lactic acid origin; the food is fortified with an active strain selected from the group consisting of Lactococcus sp. HY 49, *Lactobacillus casei* HY 2782, and *Bifidobactedum longum* HY 8001, preferably a combination of all three, optionally in combination with antibodies obtained in the yolk of an egg of a hen immunized against a pathogenic factor selected from the group consisting of fractionated *H. pylori* and urease of *H. pylori*. "Fractionated *H. pylori*" consists essentially of a pathogenic factor selected from the group consisting of *H. pylori*-urease (hereafter referred to only as "urease"), flagella of *H. pylori* and outer membrane of *H. pylori* separated from the rest of the mass of *H. pylori* cells. Portions (ii) and (iii) are typically used together (referred to as "flagella/outer membrane") to avoid the effort of separating them, were each to be used individually. Urease, though not an integral portion of the *H. pylori* cells is referred to as a constituent of fractionated *H. pylori* because it is derived from, and separated from the comminuted cells.

It is a specific object of this invention to provide an improved food selected from the group consisting of a conventional food of lactic acid bacterial origin and a non-conventional food, in combination with an effective dosage amount of an active strain selected from the group consisting of Lactococcus sp. HY 49, *Lactobacillus casei* HY 2782, and *Bifidobacterium longum* HY 8001, said conventional food being selected from the group consisting of yogurt, buttermilk, cream cheese and ice cream, and said non-conventional food being a nutritional yogurt drink. The useful concentration of active lactic acid bacteria strain(s) in the food is in the range from about $1\times10^8$ cfu/ml to about $1\times10^{10}$ cfu/ml, preferably in the range from $5\times10^8$ cfu/ml to about $5\times10^{10}$ cfu/ml, and optimally about $1\times10^9$ cfu/ml in a unit serving. The useful concentration of H. pylori-antibodies in egg yolk is in the range from 50 mg to about 250 mg per unit serving, typically in yogurt. The egg yolk is typically used in a fortified food in the range from about 0.05% to about 4% by weight of the food, preferably in the range from 0.5 to 2%, so that at 2% the food contains less than 125 mg of antibodies.

It is another general object of this invention to provide a method of preventing and/or treating disorders associated with infection by H. pylori, the method comprising administering to a human a nutritional food in combination with an effective dosage amount of one or more of the active strains identified immediately hereinabove, in plural successive unit servings, each unit serving spaced apart from a prior one by a period in the range from 1 hour to 3 days; and, preferably to do so in combination with egg yolk powder containing H. pylori-antibodies derived from one or more of the afore-specified pathogenic factors, most preferably all three in combination, wherein the antibodies have been stabilized with from about 5% to about 20% by weight of a water-soluble simple sugar. By a "unit serving" we refer to a conventional individual serving for the particular food being fortified; for example, for yogurt, a typical unit serving is 8 fl oz (fluid ounces) or about 450 ml, though it may range from 4 fl oz to 12 fl oz (250 ml to 950 ml). The term "simple sugar" refers to a carbohydrate containing an α-hydroxy aldehyde or an α-keto primary alcohol, preferably sucrose, fructose, lactose, glucose, dextrose and the like.

It is another specific object of this invention to provide a novel adjuvant which is more effective to potentiate an immune response to H. pylori antigens than conventionally used Freund's adjuvant (complete or incomplete) and which not only produces more antibodies than with conventional adjuvants, but also produces more than 75% of the antibodies in the yolk of a hen immunized with an antigen of fractionated H. pylori in the novel adjuvant.

BRIEF DESCRIPTION OF THE DRAWING

The foregoing and additional objects and advantages of the invention will best be understood by reference to the following detailed description, accompanied with schematic illustrations of preferred embodiments of the invention, in which illustrations like reference numerals refer to like elements, and in which.

DETAILED DESCRIPTION OF PREFERRED EMBODIMENTS

Figure 1:
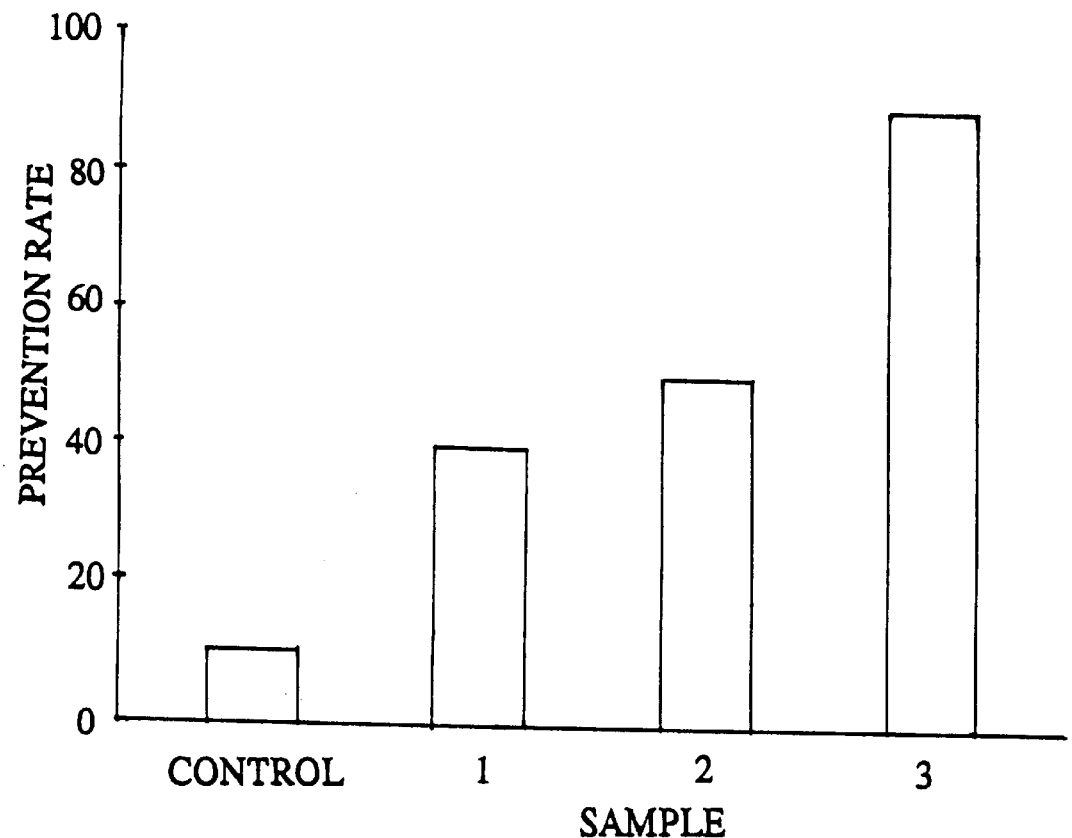
FIG. 1 shows four bars in a graph, the first, second, third and fourth bars each showing the "infection inhibition rate" or prophylactic properties attributable to (i) a control, (ii) combined fractionated H. pylori-antibodies, (iii) lactic acid bacteria Lactococcus sp. HY 49, Lactobacillus casei HY 2782, and Bifidobactetium longum HY 8001, combined, and (iv) the combination of fractionated H. pylori-antibodies and combined lactic acid bacteria, respectively. The rate is depicted as "percentage of infection free mice" along the vertical axis; the samples being compared are depicted along the horizontal axis.

Screening of non-toxic bacteria for effectiveness against H. pylori:

A test procedure for finding bacteria which, by themselves, are effective in vitro is as follows—H. pylori was cultured for 2 days in a stock commercially available Brucella broth containing 5% bovine fetal serum. Several kinds of lactic acid bacteria cultures, and those of bacteria closely related to lactic acid bacteria, all kept in stock, were similarly cultured for 2 days and filtered with a 0.45 μm filter to provide a test culture having about the same concentration (cfu/ml) of cells as the H. pylori cultured for 2 days. A procedure analogous to the Test Procedure described above on page 4 is used to find which strains of which bacteria form a substantial inhibition ring. By "substantial inhibition" is meant that the area of the annular zone of inhibition is at least as great as the area of a circle into which the test culture is deposited. Though several strains were found to provide some inhibition, those which provided substantial inhibition were: Lactococcus sp. HY 49 (patent file #94-22715, applicant: Korea Culture Collection, application number: KFCC 10842), Lactobacillus casei HY 2782 (patent file #93-26829, applicant: Korea Culture Collection, application number: KFCC 10803), and Bifidobacterium longum HY 8001 (patent file #95-30301, applicant: Korea Culture Collection, application number: KFCC 10870).

Four cylinders, each 8.1 mm in diameter, are set on a plate and 25 ml Brucella agar is poured around the peripheries of the cylinders and congealed. 170 μl (microliters) of a suspension of H. pylori ($10^9$ cfu/ml) in 3 ml of Brucella broth is added to the Brucella agar by pouring it over the surface of the congealed agar. The cylinders were removed and the plate cultivated in a microaerophilic atmosphere at 37° C. to produce a lawn of H. pylori around four 8.1 mm diameter circles left by the removed cylinders. Then 170 μl of a liquid culture of lactic acid bacteria (cultivated for two days) is deposited within each circle. After cultivating the bacteria on the plate for 24–48 hr, the inhibition zone is recognized as the diameter of the zone around the periphery of each circle. A visible growth of H. pylori at the circumference of each circle is evidence of no visible inhibition, that is, the diameter of the circle is 8.1 mm; and, the larger the diameter of the inhibition zone, the more effective is the strain of bacillus tested.

TABLE 1

| Strain | Average |
| --- | --- |
| L. casei Hy 2226 | 9.8 ± 0.5 |
| L. casei Hy 2472 | 9.2 ± 0.3 |
| L. casei Hy 2782 | 14.5 ± 0.4 |
| L. acidophilus Hy 2101 | 9.5 ± 0.3 |
| L. acidophilus Hy 2104 | 12.3 ± 0.4 |
| L. acidophilus Hy 2109 | 11.9 ± 0.6 |
| L. acidophilus Hy 2115 | 9.8 ± 0.5 |
| L. acidophilus Hy 2125 | 8.1 ± 0.4 |
| L. gaseri Hy 2392 | 9.8 ± 0.3 |

TABLE 1-continued

| Strain | Average |
| --- | --- |
| L. cryspatus Hy 2330 | 8.8 ± 0.4 |
| L. brevis Hy 2705 | 9.3 ± 0.5 |
| L. planetarium Hy 2707 | 13.6 ± 0.5 |
| L. planetarium Hy 2355 | 11.2 ± 0.6 |
| L. lactis Hy 2229 | 8.4 ± 0.3 |
| L. sp. Hy 498* | 14.8 ± 0.4 |
| Bifidobacterium longum Hy 2177 | 9.2 ± 0.6 |
| Bifidobacterium longum Hy 8001 | 12.3 ± 0.4 |
| Bifidobacterium longum Hy 2640 | 8.8 ± 0.6 |

*better identification of species and strain not currently available

In addition to commonly ingested foods, the bacteria and/or antibodies may be delivered in an oral liquid medicine to a patient suffering from duodenal and gastric ulcers, or to one recovering from a stomach or duodenum operation, or to one who simply has an upset stomach. Humans who have been consuming (a) one or more of the identified active strains in an amount in the range stated above; or, (b) the combination of one or more of the identified active strains in the stated amount, with yogurt in the stated amount, have shown no sign of gastritis or of gastric or duodenal ulcers. For example, a unit serving of 100 ml of yogurt contains from 0.5 gm to about 2 gm of egg yolk containing antibodies in the range from 10 mg to 40 mg. The results for the treatment of humans with ulcers are not currently available as the tests are in progress.

Antibodies obtained from fractionated H. pylori in combination with one or more of the foregoing active strains of bacteria produce additive results in efficacy against H. pylori, and in some instances produce unexpectedly enhanced results. The beneficial effects of the bacteria and/or the antibodies are best experienced when combined with yogurt, ice cream, infants' formula, and foods after they have been formulated, so as not to be subjected to a temperature which will inactivate the bacteria.

Foods, fortified with the live bacteria and/or egg yolk, may be any conventional food for humans, but is preferably of lactic acid bacterial origin, such as yogurt, buttermilk, cream cheese and ice cream. The fortified food may also be a non-conventional food produced from natural products by physical and chemical modification, for example, an acceptable alternative for yogurt which mimics the characteristic milky taste and mouth-feel of drinkable yogurt while providing supplemental nutrition in the form of protein, carbohydrate, fat, vitamins and minerals in each serving. One particular example of a non-conventional food is liquid or frozen yogurt prepared by combining sources of fat and milk-derived solids with a relatively undenatured whey protein concentrate to form a mixture having no more than 2 parts casein to 1 part whey protein, as described more fully in U.S. Pat. No. 4,110,476, the disclosure of which is incorporated by reference thereto as if fully set forth herein. Another particular example of a non-conventional food is a protein-containing nutritional supplement containing from 1 to 10% by weight of whey protein isolate, at least one source of carbohydrate, vitamins, trace minerals and ultra trace minerals, as described more fully in U.S. Pat. No. 5,641,531, the disclosure of which is incorporated by reference thereto as if fully set forth herein.

Manufacture of Antibody:

H. pylori-antibodies are obtained in the yolks of eggs from hens vaccinated with either one or more of the constituents of fractionated H. pylori. The hens are white Leghorns, 30–50 weeks old, vaccinated by muscle shot or injection. Antigens of fractionated H. pylori were obtained from H. pylori ATCC43504 and also from infected patients (KS 51). In the tests described hereunder, the KS 51 was used because they were easier to cultivate.

A specific oily vaccination-promotive adjuvant is used rather than the Freund's complete or incomplete adjuvant of the prior art, mainly because the novel oily adjuvant provides better production of antibodies on a large scale, concentrates the antibodies in the egg yolk, both of which make production of the antibodies unexpectedly economical. This novel adjuvant consists essentially of an emulsifier mixed with Drakeol®, a type of mineral oil. The emulsifier was produced by mixing Span® 85 and Tween® 85 in a ratio in the range from about 40:60 to about 60:40, most preferred being 54:46. A mixture of Drakeol®, emulsifier, and antigen in a ratio in the range from about 5:1:4 to about 13:1:12, optimally 9:1:8, respectively, was emulsified.

Hens are vaccinated four times, each successive vaccination spaced apart from a prior one by an interval of 2 weeks, until a sufficiently high level of desired antibodies is obtained. The characteristic value of antibodies transferred to an egg was measured by the Enzyme Immune Absorption method, or by the Microtiter method.

Whole egg powder and egg yolk aqueous protein powder, each containing antibodies, and purified antibodies obtained therefrom, are manufactured by monitoring the changes of antibody value by Microtiter after vaccinations of hens at 1 week intervals, and taking an egg when it shows a sufficiently high (increased) value of antibody.

Production of Powder from Aqueous Egg Yolks Containing Antibodies:

The separation of antibodies may be done by any conventional antibody-separating method, it being preferred to separate the egg yolks from the albumen, and homogenizing them in a Homo-Mixer in about a four-fold volume of distilled water. The antibody value of the mixture, determined by Microtiter in the range from 30 to 200, typically about 100. Then 2 mg of lambda carrageenan is added for each ml of homogenized mixture and shaken before allowing the mixture to stand for 30 min. Thereafter the mixture is centrifuged at 10,000×g for 10 min. The supernatant liquid is filtered through filter paper and the filtrate is concentrated to one-tenth of its volume by removing 90% of the liquid as permeate through an ultra-filtration membrane which allows only those molecules having a molecular weight lower than 30,000 to pass through the membrane. The concentrate is then freeze dried to yield a powder of water-soluble proteins which contain desired antibodies.

Production of Purified Antibodies from Egg Yolks Powder:

The freeze-dried powder obtained above was dissolved in distilled water and passed through an ion-exchange column in which the antibodies are separated from the egg yolk. The antibodies are then eluted from the column to provide a solution of purified antibodies. Alternatively, purified antibodies may be obtained from aqueous egg yolk protein by any other conventional method such as liquid chromatography, affinity chromatography, etc. The purified antibodies are obtained by vacuum drying the solution of purified antibodies.

Selection of Lactic Acid Bacteria According to their Effect on H. pylori:

H. pylori was grown as a lawn on Brucella medium in a microaerophilic environment. Numerous species and strains of cultivated lactic acid bacteria are screened for activity by dropping them on the lawn, and only those were selected which visibly, substantially inhibited growth of the H. pylori. The selection process yielded the above-identified active strains of bacteria, which were cultivated for use either individually or in combination, one with another. For brevity, the strains are hereafter referred to as HY 49 (obtained from patent file #94-22715, applicant: Korea Culture Collection, application number: KFCC 10842); HY 2782 (obtained from patent file #93-26829, applicant: Korea Culture Collection, application number: KFCC 10803); and HY 8001 (obtained from patent file #95-30301, applicant: Korea Culture Collection, application number: KFCC 10870); and, as tested, HY 49 showed the highest activity.

In the following illustrative examples all "parts" refer to "parts by weight" unless stated otherwise.

Example 1

A. Preparation of Flagella/Outer-membrane Antigen:

A broth of *H. pylori* (KS 51) obtained from a patient was cultivated in a microaerophilic atmosphere (3% –5% oxygen, 10% carbon dioxide, remainder nitrogen) at 37° C. for 2 days using Brucella medium containing 5% serum of cow's fetus, and the culture concentrated by centrifuging it at 4000×g for 20 min. This concentrate of cultured cells was collected and suspended in phosphate physiological salt buffer. The concentrate was disintegrated (by sonication) and centrifuged at 10,000×g for 20 minutes so as to discard the larger particles. The obtained supernatant layer was then centrifuged at 100,000×g for 30 mins to separate a pellet of wanted flagella and outer membrane from a supernatant layer which contains the urease.

B. Preparation of Urease Antigen:

A concentrate of cells cultured, collected, sonicated and suspended in phosphate physiological salt buffer in a manner described immediately hereinabove was flowed through a DEAE-Sephacel anion-exchange column, washed with phosphate physiological salt buffer (pH 6.8) of 20 mM, and then eluted with a 1.0 M NaCl solution (density distribution method). Samples adsorbed in successive sections of the column are collected. The absorption of each section was measured at a wavelength of 280 nm (nanometers) and the sample with the highest absorption was verified by the urease test method. This sample was dialyzed with the same buffering solution, concentrated using an ultra filter membrane, and the filtered concentrate used as an antigen.

Example 2

Manufacture of *H. pylori*-antibodies in Eggs:

The flagella is not separated from outer membrane in Example 1 above, because separation is difficult; it is also needlessly expensive to separate proteins of similar molecular mass. Flagella/outer membrane antigen obtained in Example 1 was mixed with the novel adjuvant and shot by intramuscular injection into the pectoral muscles of white leghorn hens 40 weeks old, at intervals of 2 weeks until a sufficiently high level of antibody was obtained. The concentration of flagella/outer membrane in the adjuvant is in the range from 60 mg/ml to 200 mg/ml, typically about 100 mg/ml; and typically 1 mg/ml in 1 ml is injected each time.

The characteristic value of antibody transferred into an egg was measured using Microtiter method as follows.

The aqueous protein fraction of egg yolk containing antibodies obtained as described above from eggs collected every 2 weeks, is mixed with an aqueous solution of lambda carrageenan (0.15% w/v) so that there is 1 g of lambda carrageenan in 9 ml of the mixture. The mixture is left at room temperature (20° C.) for 30 minutes, and then centrifuged at 10,000×g for 10 min to provide a supernatant solution. This solution was diluted with saline phosphate buffering solution (PBS, pH 7.4) to provide numerous samples at various dilutions, represented as $2^n$ diluted test samples. 50 $\mu l$ (microliter, that is, $10^{-6}$ liter) of each test sample is mixed with an equal volume (50 $\mu l$) of sonicated bacteria and smeared on a microplate which is maintained at 37° C. for 24 hours, after which each test was checked for agglutination. The value of antibody agglutination was expressed as the reciprocal of the maximum dilution ratio of the sample, at which the agglutination is displayed.

Manufacture of Aqueous Protein Powder of Egg Yolk:

After separation from the eggs, yolks having an antibody agglutination value of 640 or higher are homogenized in a Homo-mixer, and mixed so as to make up 500 ml of solution with 400 ml of a lambda carrageenan (2 mg/ml) solution. After leaving this solution at the room temperature for 30 minutes, the egg yolk fatty protein was separated by precipitation using the centrifugal separation (10,000×g, 10 minutes). By filtering the supernatant through filter paper, concentrating by 10 times with an ultra-filter membrane which removes that fraction which is higher than molecular weight of 30,000, and then freeze-drying, egg yolk aqueous protein powder containing *H. pylori*-antibodies is obtained.

Example 3

Measuring Antibody Value of Three Pathogenic Factors in Combination:

A sample was formulated by combining 200 $\mu g$ of urease; 400 $\mu g$ of outer-membrane; and 400 $\mu g$ of flagella, with an equal weight of oily adjuvant. 1 ml of this sample was injected into 30 week old white leghorn hens, and the level of antibodies stimulated were measured at various intervals over 14 weeks. The production of antibodies was measured by the Microtiter method. The results obtained are set forth in Table 2 below.

TABLE 2

| Period after injection (weeks) | Antibody value (measured by Microtiter) |
| --- | --- |
| 0 | >20 |
| 1 | 40 |
| 2 | 80 |
| 3 | 160 |
| 4 | 320 |
| 6 | 640 |
| 8 | 1280 |
| 10 | 1280 |
| 12 | 1280 |
| 14 | 640 |

As evident from the above, the antibody value reaches a maximum after about 8 weeks and diminishes after about 14 weeks.

Example 4

Mutine Adherence Inhibition Test

The prophylactic effectiveness of several samples were compared as follows: A culture of *H pylori* $3\times10^4$ cfu/ml in broth was added to three 24 well plates each coated with 0.2% pig's stomach mucous membrane Mycine solution. To the wells of each plate was added 1 ml of the broth; then, to each plate was added 1 ml of each of three test samples A, B and C respectively, as follows:

Sample A=1 ml broth+1 ml of saline containing 1 mg of purified antibodies obtained in Example 2 (from outer-membrane+flagella)

Sample B=1 ml broth+1 ml of saline solution containing 1 mg of powdered commercially available spray-dried egg yolk containing whatever commonly present antibodies which are not destabilized.

Sample C (control)=1 ml broth+1 ml cow's serum albumen (BSA: 1 mg/ml)

After standing for 1 hour, all plates are washed with phosphate buffering solution and the number of live *H. pylori* was evaluated by measuring the urease they produced. The activity of urease was measured by the amount of ammonia produced per unit of time by the Indol-phenol method using the absorption at the wavelength of 557 nm. The results are presented in Table 3 below.

TABLE 3

| Sample identif. | number of live bacteria (%) |
|---|---|
| Sample A | 10 |
| Sample B | 90 |
| Sample C (control) | 100 |

Example 5

Manufacture of yogurt with prophylactic properties against gastritis, duodenal and gastric ulcers A combination of the active strains Lactococcus sp. HY 49+*Lactobacillus casei* HY 2782 +*Bifidobacterium longum* HY 8001, each present in about $5\times10^8$ cfu/ml, is added to freshly prepared yogurt, along with *H. pylori*-antibodies obtained from outer-membrane+flagella (as in Example 2). Addition to acidic yogurt unexpectedly minimizes the loss of antibody activity by enzyme dissolution, at the same time providing nutrition and prophylactic and therapeutic properties.

The composition of the yogurt is as follows:

TABLE 4

| Composition of Yogurt | |
|---|---|
| component | amount, % |
| cow's milk | 75.0 |
| powder cow's skim milk | 3.0 |
| fruit juice | 10.0 |
| liquid fruit sugar | 3.0 |
| hydrated crystal grape sugar | 4.0 |
| solid fruit sugar | 2.0 |
| distilled water | 3.0 |

The yogurt has a pH of about 4.

Example 6

Comparative Prophylactic Effectiveness (in mice) of Various Combinations of lactic acid bacteria and *H. pylori*-antibodies which mice were infected after being fed with each sample below:

Sample 1: yogurt+*H. pylori*-antibodies (outer-membrane+flagella) (see Example 2)

Sample 2: yogurt+all three active strains ($5\times10^8$ cfu/ml each)

Sample 3: yogurt+*H. pylori*-antibodies+all three active strains ($5\times10^8$ cfu/ml each)

Control group: yogurt only

The samples were prepared in a manner analogous to that described in Example 5.

Mice (BALB/c), albinos 4 weeks old and disease free, with normal flora and no particular sensitization to *H. pylori*, were divided into the 4 groups of 10 mice each. Each mouse in each group was fed 1 ml of a sample 3 times a day for 1 week along with their usual and regular diet. Group 1 was fed Sample 1; Group 2 was fed Sample 2; Group 3 was fed Sample 3; Group 4 was fed Sample 4. At the end of the week, the stomach of each mouse in each group was injected with 0.2 ml of a *H. pylori* KS 51 culture (about $5\times10^8$ cfu/ml) and the injection was repeated a total of three times over two days while the mice were continued to be fed as usual. The following day the mice were starved except for water. The mice were thereafter fed their regular diet along with the yogurt samples.

After 6 weeks, the mice were sacrificed and their stomachs washed with saline solution the absorption of which at 550 mn was measured (for each mouse) to determine the presence of urease; an absorption of 0.25 indicates presence of urease at low level. This level was used to determine remaining infection; that is, if absorption was less than 0.25 the mouse is deemed to have no live *H. pylori* cells. The number of mice out of 10 in each group, which showed an absorption of less than 0.25 (deemed free of infection) were then recorded. The percentage of infection-free mice is presented in FIG. 1 as a percentage, representing "prevention rate", based on 10 in each group.

The effective prevention rate is measured quantitatively in the bar graph shown in FIG. 1 in which the number of mice with a level of absorption <0.25 is plotted along the vertical axis as percent (%); the samples are identified along the horizontal axis. The control is identified under the blank portion near the intersection of the axes; for an unknown reason, one mouse remained infection-free in the control group, identified under the first bar, which group was fed with yogurt only, the other 9 mice showing an absorption above 0.25; in the group identified under the second bar, which group was fed with yogurt fortified with egg yolk containing *H. pylori*-antibodies only, 4 out of the 10 mice showed absorption less than 0.25; in the group identified under the third bar, which group was fed with yogurt fortified with the active strains 5 out of the 10 mice showed absorption less than 0.25; and in the group identified under the fifth bar, which group was fed with yogurt fortified with a combination of the active strains and the *H. pylori*-antibodies, 9 out of the 10 mice showed absorption less than 0.25. The results provide evidence that even the active strains, by themselves, provide an unexpected prophylactic effect which is greatly improved by the addition of the *H. pylori*-antibodies.

Example 7

Comparative Effectiveness of Treatment (in mice) of Various Combinations of lactic acid bacteria and *H. pylori*-antibodies which mice were infected before being fed with each sample below:

The same Samples made up in Example 6 above are used, except that the mice are first infected and then fed to measure the extent to which such treatment may have eliminated evidence of infection.

As before, 4 weeks old mice (BALB/c) were used, and they were divided into the 4 groups, every mouse having been infected with *H. pylori* KS 51 (about $5\times10^8$ cfu/ml) by injection which was repeated a total of three times over two days. The mice were then fed with the various samples over a period of one week after which they were sacrificed, and their stomachs examined as before, for urease content, the level of absorption at 550 nm being the criterion (as before), namely, absorption had to be <0.25 before a mouse was deemed essentially free of infection.

Figure 2:
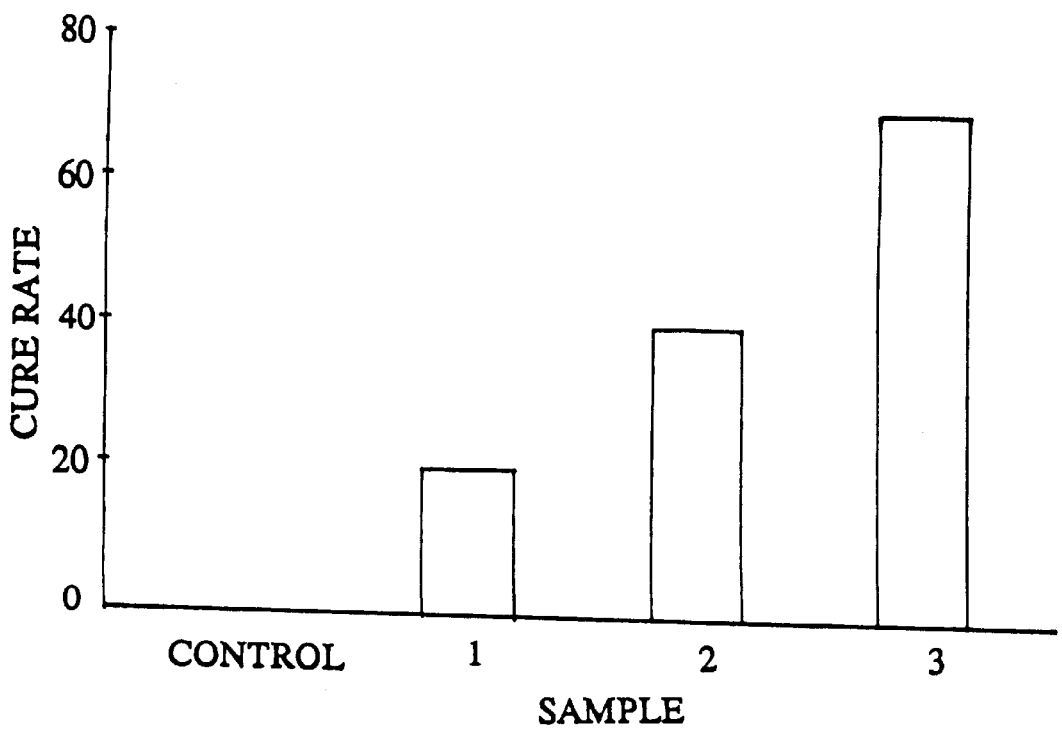
FIG. 2 shows four bars in a graph, the first, second, third and fourth bars each showing the "infection cure rate" or curative properties, attributable to (i) a control, (ii) combined fractionated H. pylori-antibodies, (iii) lactic acid bacteria Lactococcus sp. HY 49, Lactobacillus casei HY 2782, and Bifidobacterium longum HY 8001, combined and (iv) the combination of fractionated H. pylori-antibodies and combined lactic acid bacteria, respectively. As in FIG. 1, the rate is depicted as "percentage of infection free mice" along the vertical axis; the samples being compared are depicted along the horizontal axis.

The effectiveness of the treatment is measured quantitatively in the bar graph shown in FIG. 2 in which the number of infection-free mice with a level of absorption <0.25 is plotted along the vertical axis as percent (%); the samples are identified along the horizontal axis. The control is identified under the blank near the intersection of the axes;

as one would expect, every infected mouse in the control group fed with yogurt only, remained infected, all mice showing an absorption above 0.25; in the group identified under the first bar, which group was fed with yogurt fortified with egg yolk containing *H. pylori*-antibodies only, 2 out of the 10 mice showed absorption less than 0.25; in the group identified under the second bar, which group was fed with yogurt fortified with the active strains 4 out of the 10 mice showed absorption less than 0.25; and in the group identified under the third bar, which group was fed with yogurt fortified with a combination of the active strains and the *H. pylori*-antibodies, 7 out of the 10 mice showed absorption less than 0.25. The results provide evidence that even the active strains, by themselves, are unexpectedly effective in the treatment of a *H. pylori* infection, and such treatment is greatly benefitted by the addition of the *H. pylori*-antibodies.

We claim:

1. A food for general human consumption, comprising a food stored at a temperature in the range from about −45° C. but no more than 45° C., and effective to inhibit and/or prevent the growth of *Helicobacter pylori* in a human stomach, said food being fortified with an amount effective to inhibit and/or prevent the growth of *H. pylori*, of an active strain of a non-toxic living microorganism selected from the group consisting of Lactococcus sp. HY 49, *Lactobacillus casei* HY 2782, and *Bifidobacterium longum* BY 8001 said strain by itself being effective against *H. pylori* not only in vitro but also in vivo and produces bacteriocins which directly attack *H. pylori*.

2. The food of claim 1 including in addition an amount of antibodies having a Microtiter antibody titer in the range from about 30 to about 200, said antibodies being obtained from the yolk of an egg of a hen immunized against a pathogenic factor identified as urease of *H. pylori*.

3. The food of claim 2 selected from the group consisting of a conventional food of lactic acid origin and a non-conventioinal food, said conventional food being selected from the group consisting of yogurt, buttermilk, cream cheese and ice cream, said non-conventional food being a nutritional yogurt drink.

4. The food of claim 3 wherein said conventional food is yogurt.

5. The food of claim 4 wherein said active strain is Lactococcus sp. HY 49.

6. The food of claim 5 wherein said antibodies are obtained from a combination of said fractionated *H. pylori* and urease of *H. pylori*.

7. The food of claim 3 wherein said non-conventional food is a nutritional yogurt-like supplement.

8. A method of preventing and/or treating disorders associated with infection by *Helicobacter pylori*, said method comprising, administering to a human a nutritional food in combination with an active strain of a living microorganism in an amount effective to inhibit or prevent the growth of *H. pylori* in a human stomach, said living microorganism being selected from the group consisting of Lactococcus sp. HY 49, *Lactobacillus casei* HY 2782, and *Bifidobacterium longum* HY 8001, served in plural servings spaced apart by a period in the range from 1 hour to 3 days.

9. The food of claim 1 including in addition an amount of antibodies having a Microtiter antibody titer in the range from about 30 to about 200, said antibodies being obtained from the yolk of an egg of a hen immunized against a pathogenic factor identified as flagella of *H. pylori* and outer membrane of *H. pylori* separated from the rest of the *H. pylori* cells.

10. The method of claim 8 wherein said food includes an amount of antibodies having a Microtiter antibody titer in the range from about 30 to about 200, said antibodies being obtained from the yolk of an egg of a hen immunized against a pathogenic factor identified as urease of *H. pylori*.

11. The method of claim 8 wherein said food includes an amount of antibodies having a Microtiter antibody titer in the range from about 30 to about 200, said antibodies being obtained from the yolk of an egg of a hen immunized against a pathogenic factor identified as flagella of *H. pylori* and outer membrane of *H. pylori* separated from the rest of the *H. pylori* cells.

12. The method of claim 8 wherein said food is selected from the group consisting of a conventional food of lactic acid origin and a non-conventional food, said conventional food being selected from the group consisting of yogurt, buttermilk, cream cheese and ice cream, said non-conventional food being a nutritional yogurt drink.

13. The method of claim 12 wherein said conventional food is yogurt.

14. The method of claim 12 wherein said active strain is Lactococcus sp. HY 49.

15. The method of claim 13 wherein said antibodies are obtained from the yolk of an egg of a hen immunized against a pathogenic factor identified as a combination of urease of *H. pylori* and outer membrane of *H. pylori* separated from the rest of *H. pylori* cells.

16. The method of claim 12 wherein said non-conventional food is a nutritional yogurt-like supplement.

* * * * *